US005976536A

United States Patent [19]

Stephens et al.

[11] Patent Number: 5,976,536
[45] Date of Patent: Nov. 2, 1999

[54] NEISSERIA MUTANTS, LIPOOLIGOSACCHARIDES AND IMMUNOGENIC COMPOSITIONS

[75] Inventors: David S. Stephens, Stone Mountain; Charlene Marree Kahler, Decatur, both of Ga.

[73] Assignee: Emory University, Atlanta, Ga.

[21] Appl. No.: 08/512,955

[22] Filed: Aug. 9, 1995

[51] Int. Cl.[6] .......................... A61K 39/00; A61K 39/02; A61K 39/095; A01N 63/00

[52] U.S. Cl. .................................... 424/184.1; 424/200.1; 424/234.1; 424/235.1; 424/249.1; 424/250.1; 424/93.2; 424/93.21; 424/93.4

[58] Field of Search ............................. 424/184.1, 249.1, 424/250.1, 93.2, 93.21, 93.4, 200.1, 234.1, 235.1

[56] References Cited

PUBLICATIONS

Kahler et al, Proceedings of the 9th International Pathogenic Neisseria Conference, Winchester, England, 1994.

Drazek et al. (1995) "A mutation in the Neisseria gonorrhoeae rfaD homolog results in altered lipooligosaccharide expression," *Journal of Bacteriology*, 177(9):2321–2327.
Dudas, K.C. and M.A. Apicella (1988) "Selection and immunochemical analysis of lipooligosaccharide mutants of Neisseria gonorrhoeae," *Infection and Immunity*, 56(2):499–504.
John et al. (1991) "The structural basis for pyocin resistance in Neisseria gonorrhoeae lipooligosaccharides," *Journal of Biological Chemistry*, 266(29):19303–19311.
Kahler, C.M., and D.S. Stephens (1994) "Influence of lipooligosaccharide structure on the sensitivity of serogroup B Neisseria meningitidis to normal human serum," Proceedings of the Ninth International Pathogenic Neisseria Conference, Winchester, England, p. 34–35.
Kathariou et al. (1990) "Transposition of Tn916 to different sites in the chromosome of Neisseria meningitidis: a genetic tool for meningococcal mutagenesis," *Molecular Microbiology*, 4(5):729–735.
Kim et al. (1988) "Electromorphic characterization and description of conserved epitopes of the lipooligosaccharides of group A Neisseria meningitidis," *Infection and Immunity*, 56(10):2631–2638.
Lee et al. "Tn916 insertion in a galE homologue allows identification of lipooligosaccharide biosynthesis regions in pathogenic Neisseria," Abstracts, 93rd General Meeting, American Society for Microbiology, Session 299, Buffalo, New York, p. 88.
Mandrell et al. (1991) "Endogenous sialylation of the lipooligosaccharides of Neisseria meningitidis," *Journal of Bacteriology*, 173(9):2823–2832.
Mandrell et al. (1988) "Lipooligosaccharides (LOS) of Neisseria gonorrhoeae and Neisseria meningitidis have components that are immunochemically similar to precursors of human blood group antigens," *Journal of Experimental Medicine*, 168:107–126.
Sandlin et al. (1993) "Cloning of a gonococcal DNA sequence that complements the lipooligosaccharide defects of Neisseria gonorrhoeae $1291_d$ and $1291_e$," *Infection and Immunity*, 61(8):3360–3368.
Shih et al. (1995) "Identification of a second plsC homologue in Neisseria meningitidis which may be involved in lipooligosaccharide biosynthesis," Abstracts, 95th General Meeting, American Society for Microbiology, Washington, D.C., p. 206.
Lee et al. (Jul. 1995) "Microheterogeneity of Neisseria lipooligosaccharide: analysis of a UDP–Glucose 4–Epimerase mutant of Neisseria meningitidis NMB," *Infection and Immunity*, 63(7):2508–2515.
Spinola et al. (1990) "Cloning and expression in *Escherichia coli* of a Haemophilus influenzae Type b lipooligosaccharide synthesis gene(s) that encodes a 2–keto–3–deoxyoctulosonic acid epitope," 58(6):1558–1564.
Stephens et al. (1991) "Insertion of Tn916 in Neisseria meningitidis resulting in loss of group B capsular polysaccharide," *Infection and Immunity*, 59(11):4097–4102.
Stephens et al. (1994) "Tn916–generated, lipooligosaccharide mutants of Neisseria meningitidis and Neisseria gonorrhoeae," *Infection and Immunity*, 62(7):2947–2952.

Zhou et al. (1994) "Lipooligosaccharide biosynthesis in pathogenic Neisseria, " *Journal of Biological Chemistry*, 269(15):11162–11169.

*Primary Examiner*—James C. Housel
*Assistant Examiner*—V. Ryan
*Attorney, Agent, or Firm*—Greenlee, Winner and Sullivan, P.C.

[57] ABSTRACT

Provided herein are mutant strains of *Neisseria meningitidis* which produce lipooligosaccharide (LOS) differing from the wild-type LOS in structure as well as the mutant LOS molecules and immunogenic compositions containing truncated LOS molecules from a Neisseria strain containing a genetically stable in a gene selected from the group consisting of genes encoding α-1,2-N-acetylglucosamine transferase and a gene homology to an *Escherichia coli* gene encoding 1-acyl-sn-glycerol-3-phosphate acyltransferase. *N. meningitidis* NMB-559 harbors an insertion mutation in the gene encoding α-1, 2-N-acetylglucosamine transferase, and *N. meningitidis* NMB-469 harbors an insertion mutation in an nlaB gene, the protein product of which has significant amino acid sequence homology to the *E. coli* gene encoding 1-acyl-sn-glycerol-3-phosphate acyltransferase.

6 Claims, 4 Drawing Sheets

NEISSERIA MUTANTS, LIPOOLIGOSACCHARIDES AND IMMUNOGENIC COMPOSITIONS

This invention was made, at least in part with funding from the United States National Institutes of Health and the Veterans Administration. Accordingly, the United States government may have certain rights in this invention.

FIELD OF THE INVENTION

The field of this invention is the areas of vaccines and of bacterial virulence determinants, more particularly neisserial lipopoly(oligo)saccharides and incomplete or altered derivatives thereof.

BACKGROUND OF THE INVENTION

*Neisseria meningitidis* and *Neisseria gonorrhoeae* are important human pathogens. *N. meningitidis* causes meningitis, sepsis and bacteremia; *N. gonorrhoeae* causes gonorrhoea in both sexes, pelvic inflammatory disease and/or sterility in women, and rectal and pharyngeal infections, as in homosexual men. More rarely, disseminated gonococcal infection (gonococcal bacteremia) can result, with complications such as polyarthralgias or purulent arthritis, for example. These two species are relatively closely related genetically; there is approximately 85% DNA sequence homology between the genomes of the two species. The genus also includes several other species which are non-pathogenic to man although they colonize the upper respiratory tract.

The capsule of *N. meningitidis* contains N-acetylneuraminic acid (sialic acid) polymerized in α2-8 linkage; the capsule is a component which contributes to virulence in that it appears to offer at least some protection against the bactericidal activity of serum and it appears to promote invasiveness. The Group B capsule is poorly antigenic because it mimics the neural cell adhesion molecule (NCAM). It also down regulates the activation of the alternative complement pathway by enhanced binding of the complement factor II to cell surface-deposited C3b, which is subsequently inactivated by Factor I. The level of Group B capsule expression affects the virulence of the meningococci in the mouse model and the attachment of the meningococcal cells to mucosal surfaces. *N. gonorrhoeae* is not encapsulated, but extracellular polyphosphate is produced.

Neisseria produce lipopolysaccharide (LPS) which is associated with the bacterial outer membrane. The lipopolysaccharide differs from that of the Enterobacteriaceae in that there are short, often branched sugar chains rather than relatively long repeating subunits. Hence, the neisserial LPS is known as lipooligosaccharide (LOS). Neisserial LOS is classified into six serotypes among the gonococci and into thirteen in the meningococci. Neisserial LOS contain glucose, galactose, 3-keto-2-deoxyoctanoic acid (KDO), glucosamine, galactosamine, sialic acid and ethanolamine in ratios and linkages which depend on the serotype. LOS molecules generally have molecular masses in the range of about 3200 to about 7000, as estimated by sodium dodecyl sulfate polyacrylamide gel electrophoresis (SDS PAGE). The short, often branched oligosaccharide chains are attached via KDO to lipid A embedded in the outer membrane. The LOS structure of a particular strain is subject to antigenic variation.

The lipid A acts as a classic endotoxin and can induce changes in the permeability of the blood brain barrier after invasion of the cerebrospinal fluid during meningococcemia [Tunkel and Scheld (1993) *Clin. Res. Microbiol.* 6:118–136]. The composition of the LOS influences the invasive capacity of the meningococci [MacKinnon et al. (1993) *Microb. Path.* 15:359–366] and in the gonococci as well as the meningococci, the composition of the LOS affects the susceptibility of the bacterial cells to normal human serum [Shafer et al. (1984) *J. Infec. Dis.* 149:179–183; Porat et al. (1995) *Infect. Immun.* 63:2164–2172].

The terminal galactose of neisserial lipooligosaccharide is sialylated. The wild-type LOS lacto-N-tetraose unit of eight of the twelve serotypes of *N. meningitidis* appears to mimic certain human blood group antigens [Mandrell et al. (1988) *J. Exp. Med.* 168:107–126; Tsai and Civin (1991) *Infect. Immun.* 59:364–369]. Phase variation can produce heterogeneous oligosaccharide chains, and therefore a change in the antigenic profile of the strains. In gonococci, attachment of the sialic acid to the terminal galactose found in many of the LOS immunotypes results in increased resistance to the bactericidal action of normal human serum. Accordingly, in the formulation of vaccine compositions, it is important to avoid triggering an autoimmune response in the vaccinated individual.

While purified polysaccharides from Groups A and C meningococci have been used successfully in vaccines, the polysaccharides of the Group B meningococci are poor antigens, per Davis et al. (1990) *Microbiology and Immunology,* J. B. Lippincott Company, Philadelphia, Pa., at page 558.

There is a long felt need in the art for a protective vaccine effective in the prevention of human diseases caused by the pathogenic Neisseria species, *N. gonorrhoeae* and *N. meningitidis,* especially Group B meningococci. Meningococcal meningitis or meningococcemia can result in about 85% mortality if untreated and about 10–20% if treated, and those with deficiencies in late complement cascade components C5, C6, C7 and C8 appear to be prone to multiple episodes of meningococcal meningitidis. For example, non-pathogenic strains or antigenic material therefrom, particularly those which lack intact lipooligosaccharide (LOS) structure, as antigen for preparing antibodies specific to this bacterial surface component or for vaccines useful in protection against the neisserial disease resulting from infection with Neisseria species.

SUMMARY OF THE INVENTION

An object of the present invention is to provide *Neisseria meningitidis* mutant strains which produce incomplete lipooligosaccharides (LOS) due to genetically stable mutations in genes encoding LOS biosynthetic enzymes or enzymes responsible for the synthesis of LOS precursors. Specifically exemplified herein are two mutant strains of *N. meningitidis* NMB: NMB-469 which has a stable insertion mutation in a gene termed nlaB, the product of which has significant amino acid sequence homology to the gene known as plsC in *E. coli*; the *E. coli* gene encodes 1-acyl-sn-glycerol-3-phosphate acyltransferase, an enzyme involved in phospholipid synthesis; NMB-559 has a stable insertion mutation in the gene encoding α-1,2-N-acetylglucosamine transferase, which attaches N-acetylglucosamine to the inner core of the LOS.

Also provided by the present invention are LOS preparations characterized in that the LOS molecules are structurally incomplete (i.e., truncated) relative to the LOS prepared from the wild-type parent strain *N. meningitidis* NMB. The LOS of *N. meningitidis* NMB-469 differs from the wild-type in lacking any oligosaccharide side chain distal to the KDO moieties, and the LOS of N. meningitidis NMB-559 differs from the wild-type LOS in that it lacks the N-acetylglucosamine and other sugars distal to the heptose units attached to the KDO moieties, which, in turn, are attached to the lipid A (see FIG. 1).

It is an additional object of the invention to provide cloned DNA molecules which can be used to introduce genetic defects in LOS biosynthesis into other strains of N. meningitidis, N. gonorrhoeae or Hemophilus influenzae. The cloned DNA fragment containing the stable Tn916 insertion in the rfaK gene (derived from N. meningitidis NMB-559) can be used to introduce the same genetic defect into other strains to produce novel immunotypes. The cloned DNA fragment containing the stable Tn916 insertion in the nlaB gene (derived from N. meningitidis NMB-469) can be used to introduce the same genetic defect into other strains to produce novel immunotypes in which the lipid A moiety is altered as compared with the parental counterpart strain. Alternatively, null mutations other than the exemplified transposon insertions can readily be made and utilized without the expense of undue experimentation by the skilled artisan using the teachings of the present disclosure, together with what is well known in the art.

Compositions and immunogenic preparations including but not limited to vaccines, as specifically exemplified, comprising at least one lipooligosaccharide preparation derived from one of N. meningitidis NMB-469 and N. meningitidis NMB-559 and a suitable carrier therefor are provided. Alternatively, the immunogenic composition can comprise cells of at least one of the specifically exemplified N. meningitidis NMB-469 and N. meningitidis NMB-559 strains and a suitable carrier. It is understood by one of ordinary skill in the art that other, functionally equivalent, strains of N. meningitidis, for example, NMB, can be produced by the introduction of the cloned DNA containing the insertion mutations responsible for the phenotypes of the 469 and 559 mutants. It is also within the scope of the present invention and readily within the grasp of the ordinary skilled artisan to generate other types of genetically stable mutations in the rfaK and/or nlaB genes of N. meningitidis and/or N. gonorrhoeae and/or H. influenzae. Such immunogenic compositions (or vaccines) are useful, for example, in immunizing an animal, especially humans, against neisserial disease resulting from infection by pathogenic neisserial species, particularly Neisseria gonorrhoeae and Neisseria meningitidis. Such immunogenic compositions can also elicit the production of antibodies which will cross react with LOS of Hemophilus influenzae strains expressing epitopes in common with those of the starting N. meningitidis strain(s). The immunogenic preparations comprise an immunogenic amount of a non wild-type lipooligosaccharide from strain of N. meningitidis or N. gonorrhoeae, or an immunogenic fragment thereof, or of cells of one or more strains of Neisseria which lack an intact lipooligosaccharide. Such immunogenic compositions advantageously further comprise lipooligosaccharide(s) or neisserial cells of one or more other serological types, including, but not limited to, any known to the art, among which are serogroups A, B, C, D, E, H, I, K, L, W-135, X, Y and Z [Apicella, M. (1995) "Neisseria meningitidis," in Principles and Practice of Infectious Disease (4th edition), Eds. G. L. Mandell, J. E. Bennett and R. Dolin, Churchill Livingstone Inc., p. 1896]. It is understood that where whole cells are formulated into the immunogenic composition, the cells are preferably inactivated, especially if virulent. By "immunogenic amount" is meant an amount capable of eliciting the production of antibodies, preferably conferring protective immunity directed against pathogenic N. gonorrhoeae or N. meningitidis and certain strains of H. influenzae in an individual to which the vaccine has been administered.

An additional aspect of the present invention is the coding sequence, given in SEQ ID NO:1, of the N. meningitidis rfaK gene which has been inactivated in strain NMB-559; the deduced amino acid sequence of the protein of this gene is provided in SEQ ID NO:2.

A further aspect of the present invention is the coding sequence, given in SEQ ID NO:3, of the N. meningitidis nlaB gene, corresponding to that which is inactivated in strain NMB-469; the deduced amino acid sequence is provided in SEQ ID NO:4. It is noted that the deduced amino acid sequence begins with the 5'-most of 4 methionine residues of the open reading frame. Without wishing to be bound by any particular theory, it is postulated that the protein product of the nlaB gene begins with the first Met given in SEQ ID NO:4.

DETAILED DESCRIPTION OF THE INVENTION

Abbreviations used herein for lipooligosaccharide components are standard in the art: X represents a sugar residue that has not yet been identified but may be any sugar residue including but not limited to phosphorylated sugars, amino sugars and acetylated sugars and sugar acids. The abbreviations for sugar residues as used herein are as follows: Gal, galactose; Glc, glucose; GlcNAc, N-acetylglucosamine; KDO, 3-keto-3-deoxyoctanoic acid (3-keto-2-deoxyoctulosonic acid; Hep, heptose; NANA, N-acetylneuraminic acid (sialic acid).

Lipooligosaccharide (LOS) is the term given to the lipopolysaccharide of Neisseria species. Unlike the lipopolysaccharide of the Enterobacteriaceae, LOS comprises relatively short oligosaccharides linked to the lipid A moiety. The structure of complete (i.e., wild-type) *N. meningitidis* LOS is given in FIG. 1. In nature this LOS is produced by pathogenic strains of *N. meningitidis*, *N. gonorrhoeae* and certain strains of *Hemophilus influenzae*. It can be purified from cells of wild-type or desired mutant strains or as a recombinant expression product using the genetically modified strains of *N. gonorrhoeae* or *N. meningitidis* or *H. influenzae*.

Figure 1:
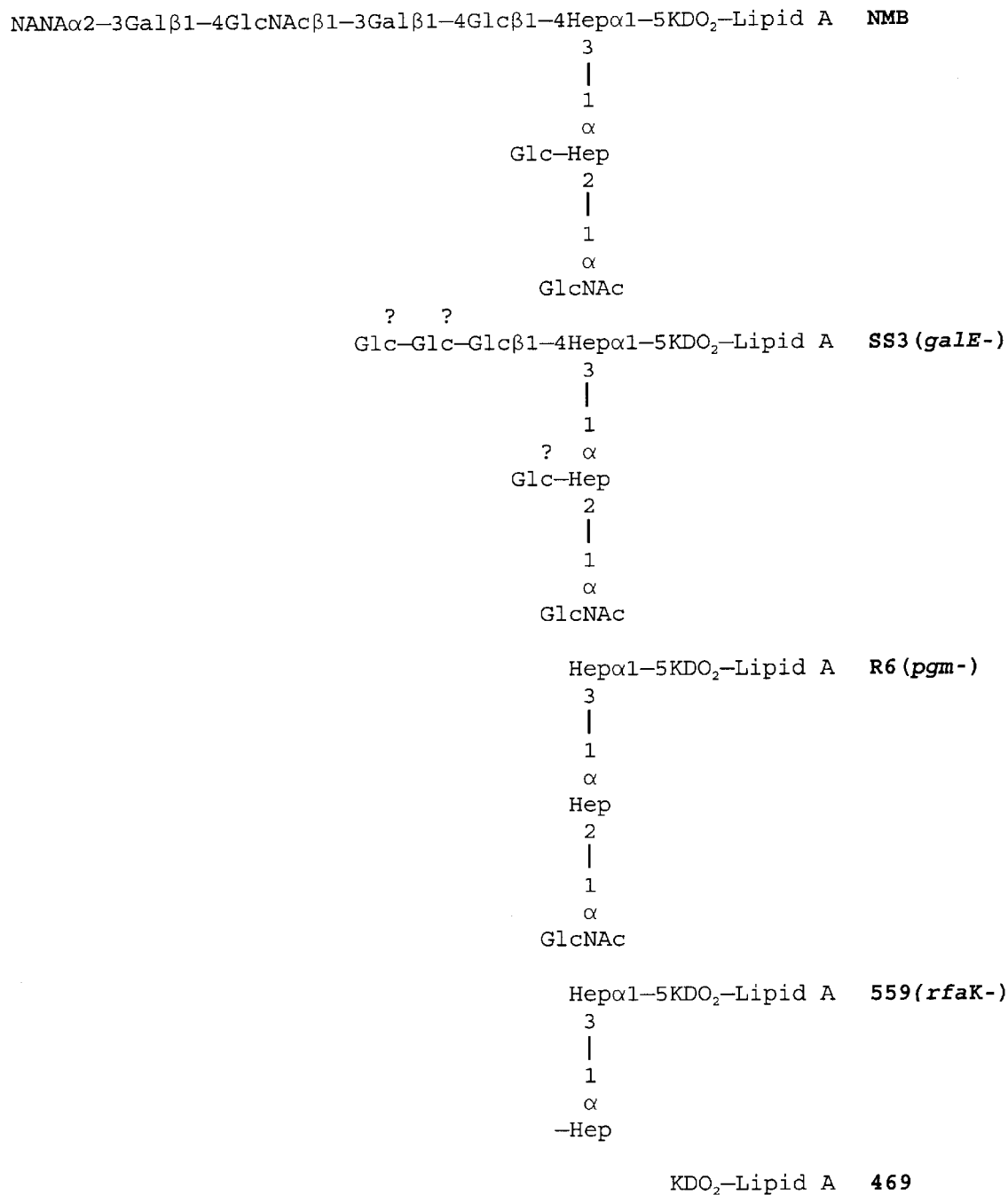
FIG. 1 is a schematic diagram of the LOS structures of the parent strain N. meningitidis NMB, and the LOS truncated mutants SS3, R6, 559 and 469. The LOS structure of NMB is similar to the L3 immunotype [Lee et al. (1995) Infect. Immun. 63:2508–2515]. Under aerobic growth conditions, about 50% of the terminal galactose resides are sialylated in the LOS of strain NMB. The SS3 mutant is deficient in UDP-glucose 4-epimerase, and the R6 mutant lacks phosphoglucomutase. The unencapsulated mutant M7 expresses a complete LOS structure except for sialyl residues. The structures of the NMB-469 and NMB-559 mutant LOS molecules have been deduced; NMB-469 contains a stable insertion mutation in the nlaB gene, a neisserial homolog of the gene known as plsC in E. coli; the E. coli gene encodes 1-acyl-sn-glycerol-3-phosphate acyltransferase, an enzyme involved in phospholipid synthesis, and NMB-559 contains an insertion in a gene encoding $\alpha$-1,2-N-acetylglucosamine transferase, which attaches N-acetylglucosamine to the inner core. The coding sequence of this gene is provided in SEQ ID NO:1; this sequence is homologous to the rfaK gene of Salmonella typhimurium. The deduced amino acid sequence of the encoded protein is given in SEQ ID NO:2.
Figure 2A:
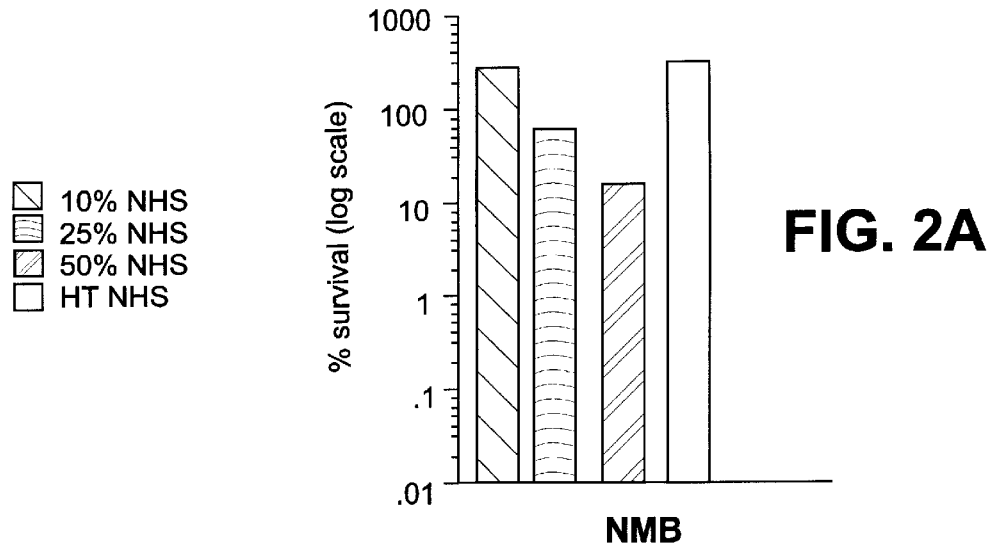
FIGS. 2A–2F illustrate the results of normal human serum (NHS) bactericidal assays for N. meningitidis NMB wild-type, and several N. meningitidis NMB LOS mutant strains. Viability was determined after 30 minutes in 10% NHS, 25% NHS, 50% NHS and heat-treated (HT) NHS. 50% NHS assays were not carried out on the 469 and 559 mutant strains.
Figure 2B:
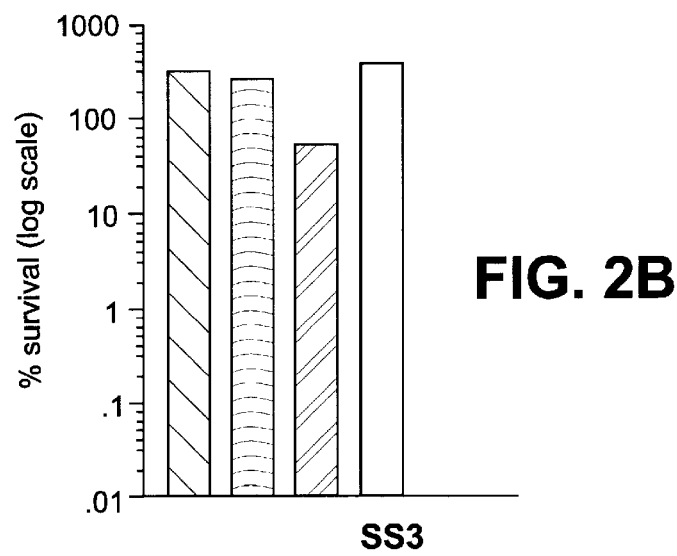
Figure 2C:
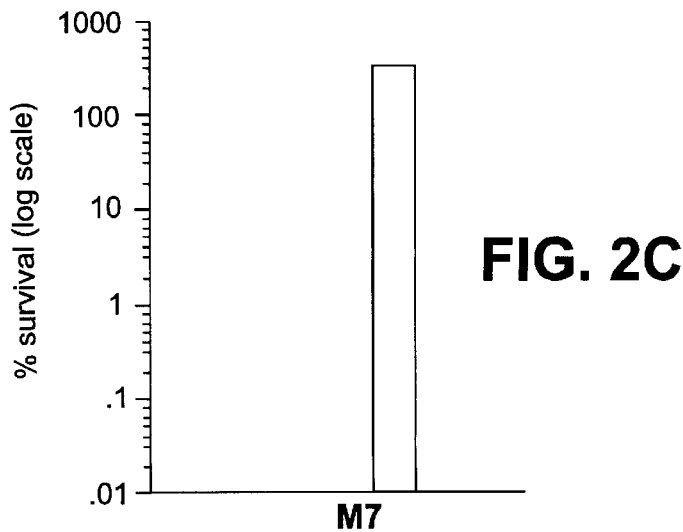
Figure 2D:
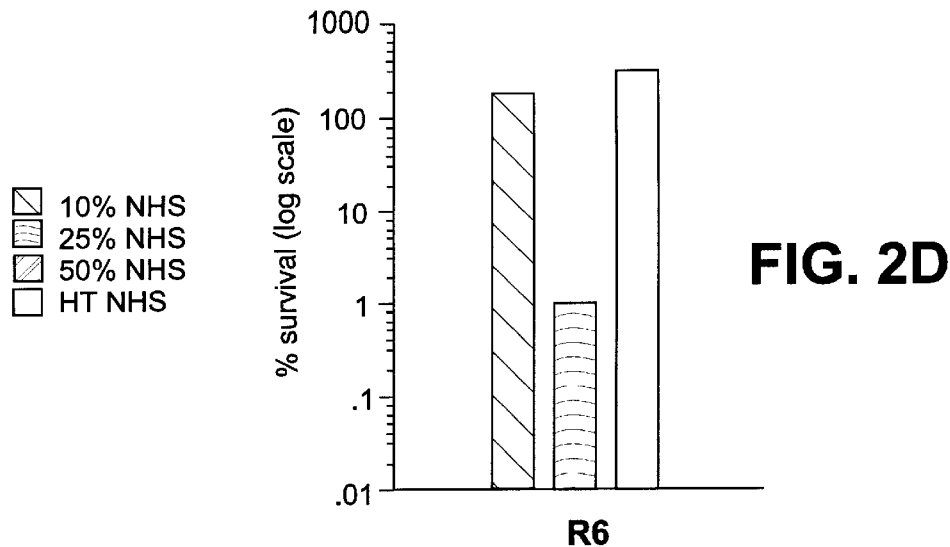
Figure 2E:
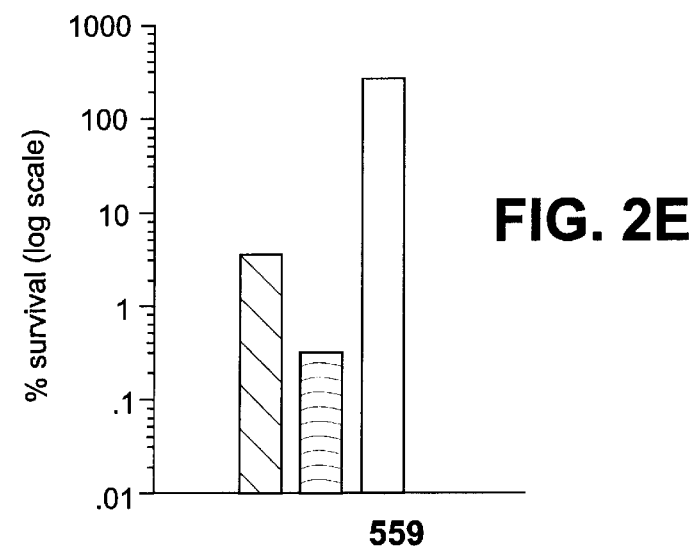
Figure 2F:
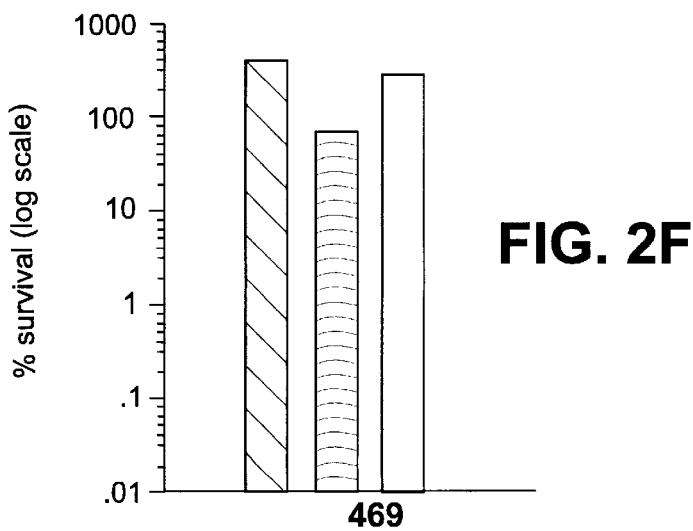
Figure 3:
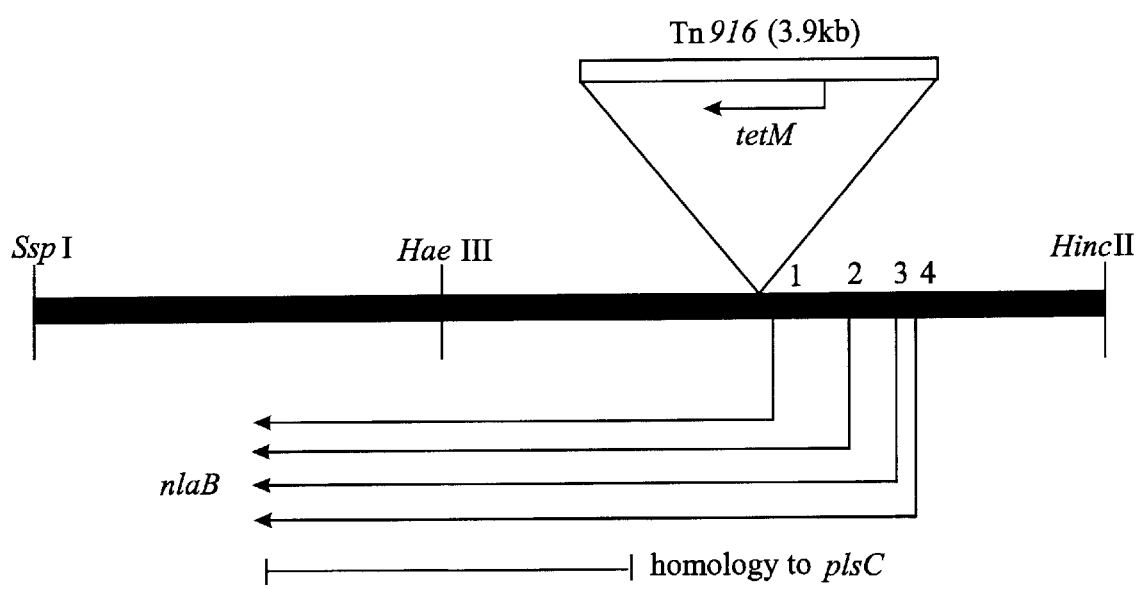
FIG. 3 illustrates the insertion site of the Tn916 in N. meningitidis strain 469. The gene which the transposon interrupts has been designated nlaB. The start site of the nlaB open reading frame has not been unambiguously identified; the four potential in-frame start sites are labeled 1, 2, 3, 4. The region of amino acid sequence homology to the E. coli plsC gene is shown by the lower line in the figure.

FIG. 1 illustrates the structures of *N. meningitidis* wild-type and certain mutant truncated LOS molecules. The wild-type LOS has an apparent molecular mass of 4.6 kDa. Strain NMB-SS3, which contains an insertion mutation in galE (UDP-4-glucose epimerase) produces an LOS of about 3.6 kDa [Stephens et al. (1994) *Infect. Immun.* 62:2947–4952]. The lacto-N-neotetraose unit appears to be replaced with two to four glucose residues. NMB-R6 produces an LOS of about 3.1–3.2 kDa which does not react with monoclonal antibody 3F11; this mutant has a Tn916 insertion in pgm, the gene encoding phosphoglucomutase. As a consequence the R6 strain cannot interconvert UDP-glucose and UDP-galactose and does not attach the oligosaccharide unit to the heptose [Zhou et al. (1994) *J. Biol. Chem.* 269:11162–11169]. Mutant NMB-559 contains a Tn916 insertion mutation in the gene homologous in sequence to the *Salmonella typhimurium* rfaK gene, which encodes α-1,2-N-acetylglucosamine transferase, which attaches GlcNAc to the inner lipid A core structure. The LOS produced by mutant NMB-559 has an apparent molecular mass of 3.0 kDa, and it lacks the α-chain sugars and the glucose and N-acetylglucosamine residues which are normally attached to the heptoses. Mutant NMB-469 contains a Tn916 insertion in nlaB, a homolog of the gene known as plsC in *E. coli*; the plsC gene encodes 1-acyl-sn-glycerol-3-phosphate acyltransferase, an enzyme involved in phospholipid synthesis. A comparison of the amino acid sequences of the *N. meningitidis* NMB nlaB and *E. coli* plsC gene products is given in Table 1. Without wishing to be bound by any particular theory, it is postulated that the lipid A moiety of NMB-469 is altered, and as a result, LOS biosynthesis is blocked. The LOS of NMB-469 is markedly truncated, with an apparent molecular mass of about 2.9 kDa and lacks reactivity with monoclonal antibody 3F11. The wild-type NMB strain and all four of the mutants whose LOS structures are illustrated in FIG. 1 produce intact capsules as determined by immunoblotting with monoclonal antibody SC1-3.

Previous studies have established the importance of LOS in the resistance of *N. gonorrhoeae* to complement-mediated killing by normal human serum (NHS) [Shafer et al. (1984) *J. Inf. Dis.* 149:175–183]. To determine the relative roles of the group B capsule and LOS in resistance of *N. meningitidis* to NHS, the truncated LOS mutants NMB-R6, NMB-SS3, NMB-569 and NMB-469 were examined in comparison to the wild-type NMB. The capsule-deficient mutant NMB-M7 was also tested. NMB-M7 contains a Tn916 insertion is the synX gene, which encodes either N-acetyl-D-glucosamine-6-phosphate-2-epimerase or the N-acetyl-mannosamine-6-phosphate phosphatase. This strain produces LOS which has no sialylation [Swartley and Stephens (1994) *J. Bacteriol.* 176:1530–1534]. The results of the serum killing tests are shown in FIGS. 2A–2F. An initial time point assay using the 10%, 25% and 50% NHS revealed that NMB, NMB-SS3 and NMB-469 behaved similarly in these experiments. Therefore, the LOS mutations in SS3 and 469 did not appear to result in enhanced killing by factors in NHS. It is noted that NMB-469 appears to produce fewer viable cells per unit volume [colony forming units per ml (cfu/ml)] than the parental strain. This strain has a defect in a gene whose product is involved in the synthesis of the phospholipid portion of LOS. The unencapsulated mutant NMB-M7 did not survive any serum concentration. The LOS mutants NMB-R6 and NMB-559 were more sensitive to 25% NHS than the parental NMB, but the differences were not statistically significant. Mutant NMB-559 appeared more sensitive to 10% NHS than the parent as well. All of these strains survived in heat-treated NHS (treated at 60° C. for 30 min), suggesting that the mechanism for killing in these assay was complement-mediated. FIGS. 2A–2F graphically illustrate the serum responses of the *N. meningitidis* NMB wild-type and mutant strains. Thus, the integrity of the group B capsule appears to be the most important factor in determining serum sensitivity for meningococcal strain NMB. However, certain alterations in LOS structure can modulate serum sensitivity in an encapsulated background.

A chemically synthesized LOS is considered an "isolated" LOS preparation, as is an LOS preparation purified from cells provided that the LOS has been freed of contaminating, toxic cellular components and products.

LOS can be obtained by culturing host cells transformed with the recombinant polynucleotides comprising nucleotide sequences which direct the synthesis of a non wild-type LOS as described herein under conditions suitable to attain expression of the mutant phenotype of LOS.

The purification of wild-type LOS has been described in Galanos et al. (1969) *Eur. J. Biochem.* 9:245–249, and has been modified as described hereinbelow. Although the published purification of LOS describes the removal from the surface of cells expressing that LOS type, the present disclosure provides methods for isolating truncated LOS molecules. However, one of ordinary skill can practice the invention using modifications of the referenced procedure or the purification procedure disclosed herein and/or other modifications readily apparent to one of ordinary skill in the art.

Wild-type LOS of *N. meningitidis* NMB exhibits an apparent molecular mass of about 4.6 kDa, as determined by SDS PAGE. The structure is given in FIG. 1. It reacts with monoclonal antibody 3F11, which is specific for the lacto-N-neotetraose moiety distal to the cell surface. Cells of strain NMB also react with monoclonal antibody SC1-3, which recognizes the capsule.

Several mutant strains of *N. meningitidis* and *N. gonorrhoeae* which produce LOS distinct from that of the wild-type have been isolated, and certain of these have been described [Dudas and Apicella (1988) *Infect. Immun.* 56:499–504]. It is believed that the NMB-469 and NMB-559 mutants described herein represent novel biochemical phenotypes and novel LOS structures.

Within the present context, genetically stable means that the mutant does not revert to the wild-type phenotype at a significant frequency, preferably reversion occurs at a frequency of less than $10^{-6}$, preferably $10^{-8}$, and more preferably at a frequency of less than $10^{-10}$.

A null mutation in a particular gene is one in which no functional gene product is produced. Such a null mutation can be the result of an interruption in the coding sequence, one or more changes in the amino acid sequence such that any polypeptide synthesized therefrom does not have the function of the wild-type counterpart or it may be the result of an interruption or change in the transcriptional control sequences controlling the expression of the gene.

Techniques are available for the generation of stable insertion mutations in *N. meningitidis* and *N. gonorrhoeae*. Stephens and co-workers has described Tn916 mutagenesis of these neisserial species [Stephens et al. (1991) *Infect. Immun.* 59:4097–4102; Stephens et al. (1994) *Infect. Immun.* 62:2947–2952; Kathariou et al. (1990) *Mol. Microbiol.* 4:729–735]. Two types of insertion mutations occur: class I insertions appear to have an intact Tn916 element resulting from transposition of the transposon and class II insertions are characterized by deletion of part of the transposon with maintenance of the tetM element which confers tetracycline resistance. Insertions can be characterized in part with analysis of HaeIII-digested DNA in that Tn916 has no HaeIII sites, and the portion of the genome into which the transposon or tetracycline-resistance determining region has inserted by subcloning a HaeIII fragment with selection for antibiotic resistance. Flanking sequences can be used for sequence determination and/or for use in probe or primer for the isolation of the wild-type counterpart gene from the parental strain. When Tn916 is used to create the mutations in LOS-related genes, the Class II type of mutation is quite stable. Other types of stable mutations can be generated, including, but not limited to, deletion mutations, insertion mutations or multiple point mutations, and this may be accomplished by techniques including but not limited to oligonucleotide site-directed mutagenesis, polymerase chain reaction mutagenesis techniques, restriction endonuclease cutting and religation with or without insertion of heterologous DNA as appropriate for the type of mutation being created, as well known to one of ordinary skill in the art. The skilled artisan is capable of generating such alternate mutants using ordinary skill in the art; in particular, the DNA sequence information for rfaK provided in SEQ ID NO:1 can be employed in mutagenic strategies, and for nlaB in SEQ ID NO:3. The sequence information provided can be used to produce further mutations. It is preferred that where a transposon is used, that the resulting mutation itself is not an insertion which is further transposable.

The skilled artisan recognizes that other neisserial (and certain *H. influenzae*) strains can produce LOS with the distinguishing characteristics of a *N. meningitidis* NMB-469 or NMB-559 LOS. The distinguishing characteristics of 559-type LOS are lack of specific binding to monoclonal antibody 3F11 and an apparent molecular weight of 3.0 kDa, as estimated by SDS PAGE. An NMB-469-type LOS from a strain can be identified by lack of specific binding to monoclonal antibody 3F11 under conditions appropriate to detect specific cross-reaction and an apparent molecular weight of 2.9 kDa, as estimated by SDS PAGE. In view of the similarity of the basic structures of LOS molecules of the meningococci, gonococci and certain *H. influenzae* strains, the skilled artisan understands that an antibody, particularly a monoclonal antibody which is specific for a particular epitope, directed to a particular portion of a meningococcal LOS can be used to screen other LOS types for the presence of the epitopes recognized by that (monoclonal) antibody. It is also known that gonococcal LOS can be characterized via the sensitivity or resistance of a particular strain to certain pyocins produced by *Pseudomonas aeruginosa* [see Dudas and Apicella (1988) *Infect. Immun.* 56:499–504; John et al. (1991) *J. Biol. Chem.* 266:19303–19311 for further discussion].

A polynucleotide or fragment thereof is substantially homologous (or substantially similar) to another polynucleotide if, when optimally aligned (with appropriate nucleotide insertions or deletions) with another polynucleotide, there is nucleotide sequence identity for approximately 80% of the nucleotide bases, usually approximately 90%, more preferably about 95% to 100% of the nucleotide bases.

Alternatively, substantial homology (or similarity) exists when a polynucleotide or fragment thereof will hybridize to another polynucleotide under selective hybridization conditions. Selectivity of hybridization exists under hybridization conditions which allow one to distinguish the target polynucleotide of interest from other polynucleotides. Typically, selective hybridization will occur when there is approximately 75% similarity over a stretch of about 14 nucleotides, preferably approximately 80% similarity, more preferably approximately 85% similarity, and most preferably approximately 90% similarity. See Kanehisa (1984) *Nucl. Acids Res.*, 12:203–213. The length of homology comparison, as described, may be over longer stretches, and in certain embodiments will often be over a stretch of about 17 to 20 nucleotides, preferably 21 to 25 nucleotides, more preferably 26 to 35 nucleotides, and more preferably about 36 or more nucleotides.

The hybridization of polynucleotides is affected by such conditions as salt concentration, temperature, or organic solvents, in addition to the base composition, length of the complementary strands, and the number of nucleotide base mismatches between the hybridizing polynucleotides, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1 M, typically less than 500 mM, and preferably less than 200 mM. However, the combination of parameters is much more important than the measure of any single parameter (Wetmur and Davidson (1968) *J. Mol. Biol.* 31, 349–370).

An isolated or substantially pure polynucleotide is a polynucleotide which is substantially separated from other polynucleotide sequences which naturally accompany a native sequence. The term embraces a polynucleotide sequence which has been removed from its naturally occurring environment, and includes recombinant or cloned DNA isolates, chemically synthesized analogues and analogues biologically synthesized by heterologous systems.

A polynucleotide is said to encode a polypeptide if, in its native state or when manipulated by methods known to those skilled in the art, it can be transcribed and/or translated to produce the polypeptide of a fragment thereof. The anti-sense strand of such a polynucleotide is also said to encode the sequence.

A nucleotide sequence is operably linked when it is placed into a functional relationship with another nucleotide sequence. For instance, a promoter is operably linked to a coding sequence if the promoter affects its transcription or expression. Generally, operably linked means that the sequences being linked are contiguous and, where necessary to join two protein coding regions, contiguous and in reading frame. However, it is well known that certain genetic elements, such as enhancers, may be operably linked even at a distance, i.e., even if not contiguous.

The term recombinant polynucleotide refers to a polynucleotide which is made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Polynucleotide probes include an isolated polynucleotide attached to a label or reporter molecule and may be used to identify and isolate non-exemplified LOS biosynthetic protein coding sequences. Probes comprising synthetic oligonucleotides or other polynucleotides may be derived from naturally occurring or recombinant single or double stranded nucleic acids or be chemically synthesized. Polynucleotide probes may be labelled by any of the methods known in the art, e.g., random hexamer labeling, nick translation, or the Klenow fill-in reaction.

Large amounts of the polynucleotides may be produced by replication in a suitable host cell. Natural or synthetic DNA fragments coding for a proteinase or a fragment thereof will be incorporated into recombinant polynucleotide constructs, typically DNA constructs, capable of introduction into and replication in a prokaryotic or eukaryotic cell. Usually the construct will be suitable for replication in a unicellular host, such as yeast or bacteria, but a multicellular eukaryotic host may also be appropriate, with or without integration within the genome of the host cells. Commonly used prokaryotic hosts include strains of *Escherichia coli*, although other prokaryotes, such as *Bacillus subtilis* or Pseudomonas may also be used. Mammalian or other eukaryotic host cells include yeast, filamentous fungi, plant, insect, amphibian and avian species. Such factors as ease of manipulation, ability to appropriately glycosylate expressed proteins, degree and control of protein expression, ease of purification of expressed proteins away from cellular contaminants or other factors may determine the choice of the host cell.

The polynucleotides may also be produced by chemical synthesis, e.g., by the phosphoramidite method described by Beaucage and Caruthers (1981) *Tetra. Letts.,* 22: 1859–1862 or the triester method according to Matteuci et al. (1981) *J. Am. Chem. Soc.* 103: 3185, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

DNA constructs prepared for introduction into a prokaryotic or eukaryotic host will typically comprise a replication system (i.e. vector) recognized by the host, including the intended DNA fragment encoding the desired polypeptide, and will preferably also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

An appropriate promoter and other necessary vector sequences will be selected so as to be functional in the host. Examples of workable combinations of cell lines and expression vectors are described in Sambrook et al. (1989) vide infra; Ausubel et al. (Eds.) (1987) *Current Protocols in Molecular Biology,* Greene Publishing and Wiley Interscience, New York; and Metzger et al. (1988) *Nature,* 334: 31–36. Many useful vectors for expression in bacteria, yeast, mammalian, insect, plant or other cells are well known in the art and may be obtained such vendors as Stratagene, New England Biolabs, Promega Biotech, and others. In addition, the construct may be joined to an amplifiable gene (e.g., DHFR) so that multiple copies of the gene may be made. For appropriate enhancer and other expression control sequences, see also *Enhancers and Eukaryotic Gene Expression,* Cold Spring Harbor Press, N.Y. (1983). While such expression vectors may replicate autonomously, they may less preferably replicate by being inserted into the genome of the host cell.

Expression and cloning vectors will likely contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typical selection genes encode proteins that (a) confer resistance to antibiotics or other toxic substances, e.g., ampicillin, neomycin, methotrexate, etc.; (b) complement auxotrophic deficiencies; or (c) supply critical nutrients not available from complex media. The choice of the proper selectable marker will depend on the host cell; appropriate markers for different hosts are known in the art.

The recombinant vectors containing the LOS biosynthetic gene (or mutant gene) sequence of interest can be introduced into the host cell by any of a number of appropriate means, including electroporation; transformation or transfection employing calcium chloride, rubidium chloride, calcium phosphate, DEAE-dextran, or other substances; microprojectile bombardment; lipofection; and transfection or infection (where the vector is an infectious agent, such as a viral or retroviral genome). The choice of such means will often depend on the host cell. Large quantities of the polynucleotides and polypeptides of the present invention may be prepared by transforming suitable prokaryotic or eukaryotic host cells with LOS-related polynucleotides of the present invention in compatible vectors or other expression vehicles and culturing such transformed host cells under conditions suitable to attain expression of the desired LOS structure. The derivative LOS may then be recovered from the host cell and purified.

When it is desired to eliminate leader sequences and precursor sequences at the 5' side of the coding sequence, a combination of restriction endonuclease cutting and site-directed mutagenesis via PCR using an oligonucleotide containing a desired restriction site for cloning (one not present in coding sequence), a ribosome binding site, a translation initiation codon (ATG) and the codons for the first amino acids of the mature protein. The oligonucleotide for site-directed mutagenesis at the 3' end of the coding sequence includes nucleotides encoding the carboxyterminal amino acids of the protein, a translation termination codon (TAA, TGA or TAG), and a second suitable restriction endonuclease recognition site not present in the remainder of the DNA sequence to be inserted into the expression vector. The site-directed mutagenesis strategy is similar to that of Boone et al. (1990) *Proc. Natl. Acad. Sci. USA* 87: 2800–2804, as modified for use with PCR.

In another embodiment, polyclonal and/or monoclonal antibodies capable of specifically binding to a particular LOS phenotype or fragments thereof are provided. The term antibody is used to refer both to a homogenous molecular entity and a mixture such as a serum product made up of a plurality of different molecular entities. Monoclonal or polyclonal antibodies, preferably monoclonal, specifically reacting with LOS of a particular phenotype of interest may be made by methods known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York; and Ausubel et al. (1987) supra. Also, recombinant immunoglobulins may be produced by methods known in the art, including but not limited to the methods described in U.S. Pat. No. 4,816,567, incorporated by reference herein. Monoclonal antibodies with affinities of $10^8$ $M^{-1}$, preferably $10^9$ to $10^{10}$ or more are preferred.

Antibodies generated against the LOS phenotype of interest are useful, for example, as probes for screening DNA expression libraries or for detecting the presence of neisserial strains in a test sample. Hydrophilic regions of LOS biosynthetic enzymes can be identified by the skilled artisan, and peptide antigens can be synthesized and conjugated to a suitable carrier protein (e.g., bovine serum albumin or keyhole limpet hemocyanin) for use in vaccines or in raising antibody specific for LOS biosynthetic proteins. Frequently, the polypeptides and antibodies will be labeled by joining, either covalently or noncovalently, a substance which provides a detectable signal. Suitable labels include but are not limited to radionuclides, enzymes, substrates, cofactors, inhibitors, fluorescent agents, chemiluminescent agents, magnetic particles and the like. U.S. patents describing the use of such labels include but are not limited to Nos. 3,817,837; 3,850,752; 3,939,350; 3,996,345; 4,277,437; 4,275,149; and 4,366,241.

Antibodies specific for particular LOS phenotypes and capable of inhibiting adherence of LOS (wild-type)-expressing neisserial and/or hemophilus cells to host tissue are be useful in preventing disease resulting from neisserial and/or hemophilus infection. Such antibodies can be obtained by the methods described above.

Compositions and immunogenic preparations including vaccine compositions comprising substantially purified mutant LOS and a suitable carrier therefor are provided. Alternatively, hydrophilic regions of the LOS biosynthetic proteins can be identified by the skilled artisan, and peptide antigens can be synthesized and conjugated to a suitable carrier protein (e.g., bovine serum albumin or keyhole limpet hemocyanin) for use in vaccines or in raising antibody specific for LOS-expressing neisserial and/or H. influenzae strains. Immunogenic compositions are those which result in specific antibody production when injected into a human or an animal. Such immunogenic compositions are useful, for example, in immunizing a humans, against infection by neisserial and hemophilus pathogenic strains. The immunogenic preparations comprise an immunogenic amount of, as specifically exemplified, at least one lipooligosaccharide preparation derived from one of *N. meningitidis* NMB-469 and *N. meningitidis* NMB-559 and a suitable carrier. Alternatively, the immunogenic composition can comprise cells of at least one of the specifically exemplified *N. meningitidis* NMB-469 and *N. meningitidis* NMB-559 and a suitable carrier. It is understood by one of ordinary skill in the art that other, functionally equivalent, strains of *N. meningitidis*, for example, NMB, can be produced by the introduction of the cloned DNA containing the insertion mutations responsible for the phenotypes of the 469 and 559 mutants. It is also within the scope of the present invention and readily within the grasp of the ordinary skilled artisan to generate other types of genetically stable mutations in the rfaK and/or nlaB genes of *N. meningitidis* and/or *N. gonorrhoeae* or *H. influenzae*. Such immunogenic compositions (or vaccines) are useful, for example, in immunizing an animal, especially humans, against neisserial disease resulting from infection by pathogenic neisserial species, particularly *Neisseria gonorrhoeae* and *Neisseria meningitidis*. Such immunogenic compositions can also elicit the production of antibodies which will cross react with LOS of *Hemophilus influenzae* strains expressing epitopes in common with those of the starting *N. meningitidis* strain(s). The immunogenic preparations comprise an immunogenic amount of a non wild-type lipooligosaccharide from strain of *N. meningitidis* or *N. gonorrhoeae*, or an immunogenic fragment thereof, or of cells of one or more strains of Neisseria which lack an intact lipooligosaccharide. Such immunogenic compositions advantageously further comprise lipooligosaccharide(s) or neisserial cells of one or more other serological types, including but not limited to any known to the art. It is understand that where whole cells are formulated into the immunogenic composition, the cells are preferably inactivated, especially if the cells are of a virulent strain. Such immunogenic compositions may comprise one or more additional LOS preparations, or another protein or other immunogenic cellular component. By "immunogenic amount" is meant an amount capable of eliciting the production of antibodies directed against neisserial LOS biosynthetic proteins and against neisserial LOS, including but not limited to those of *N. meningitidis* NMB-469 and/or 559 in an animal or human to which the vaccine or immunogenic composition has been administered.

Immunogenic carriers may be used to enhance the immunogenicity of the LOS. Such carriers include but are not limited to proteins and polysaccharides, liposomes, and bacterial cells and membranes. Protein carriers may be joined to the LOS molecules to form fusion proteins by recombinant or synthetic means or by chemical coupling. Useful carriers and means of coupling such carriers to polypeptide antigens are known in the art. The art knows how to administer immunogenic compositions so as to generate protective immunity on the mucosal surfaces of the upper respiratory system, especially the mucosal epithelium of the nasopharynx, where immunity specific for *N. meningitidis* and for the remainder of the respiratory system, particularly for *H. influenzae*, and for the epithelial surfaces of the genito-urinary tract, particularly for *N. gonorrhoeae*, is most helpful.

The immunogenic compositions may be formulated by any of the means known in the art. Such vaccines are typically prepared as injectables, either as liquid solutions or suspensions. Solid forms suitable for solution in, or suspension in, liquid prior to injection may also be prepared. The preparation may also, for example, be emulsified, or the protein encapsulated in liposomes.

The active immunogenic ingredients are often mixed with excipients or carriers which are pharmaceutically acceptable and compatible with the active ingredient. Suitable excipients include but are not limited to water, saline, dextrose, glycerol, ethanol, or the like and combinations thereof. The concentration of the immunogenic polypeptide in injectable formulations is usually in the range of 0.2 to 5 mg/ml.

In addition, if desired, the vaccines may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP);N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE); and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogen resulting from administration of the immunogen in vaccines which are also comprised of the various adjuvants. Such additional formulations and modes of administration as are known in the art may also be used.

Mutant LOS and cells producing mutant LOS and/or fragments thereof may be formulated into immunogenic compositions as neutral or salt forms. Preferably, when cells are used they are of avirulent strains, or the cells are killed before use. Pharmaceutically acceptable salts include but are not limited to the acid addition salts (formed with free amino groups of the peptide) which are formed with inorganic acids, e.g., hydrochloric acid or phosphoric acids; and organic acids, e.g., acetic, oxalic, tartaric, or maleic acid. Salts formed with the free carboxyl groups may also be derived from inorganic bases, e.g., sodium, potassium, ammonium, calcium, or ferric hydroxides, and organic bases, e.g., isopropylamine, trimethylamine, 2-ethylaminoethanol, histidine, and procaine.

The immunogenic LOS preparations (or peptide antigens related thereto) compositions are administered in a manner compatible with the dosage formulation, and in such amount as will be prophylactically and/or therapeutically effective. The quantity to be administered, which is generally in the range of about 100 to 1,000 μg of protein per dose, more generally in the range of about 5 to 500 μg of protein per dose, depends on the subject to be treated, the capacity of the individual's immune system to synthesize antibodies, and the degree of protection desired. Precise amounts of the active ingredient required to be administered may depend on the judgment of the physician and may be peculiar to each individual, but such a determination is within the skill of such a practitioner.

The vaccine or other immunogenic composition may be given in a single dose or multiple dose schedule. A multiple dose schedule is one in which a primary course of vaccination may include 1 to 10 or more separate doses, followed by other doses administered at subsequent time intervals as required to maintain and or reinforce the immune response, e.g., at 1 to 4 months for a second dose, and if needed, a subsequent dose(s) after several months.

All references cited herein are hereby incorporated by reference in their entirety.

Except as noted hereafter, standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning Vol. I and II*, IRL Press, Oxford, UK; Hames and Higgins (eds.) (1985) *Nucleic Acid Hybridization*, IRL Press, Oxford, UK; and Setlow and Hollaender (1979) *Genetic Engineering: Principles and Methods*, Vols. 1–4, Plenum Press, New York. Abbreviations and nomenclature, where employed, are deemed standard in the field and commonly used in professional journals such as those cited herein.

The foregoing discussion and the following examples are provided for illustrative purposes, and they are not intended to limit the scope of the invention as claimed herein. Modifications and variations which may occur to one of ordinary skill in the art are within the intended scope of this invention.

EXAMPLES

Example 1

Bacterial Strains, Plasmids and Culture

*N. meningitidis* strain NMB (B:P1.2,5:L3,7,9) is a Group B isolate; it was originally cultured from the cerebrospinal fluid of a meningitis patient [See also Kathariou et al. (1990) *Molec. Microbiol.* 4:729–735]. Strain 269BSpec$^r$ is a spontaneous spectinomycin-resistant derivative of strain 269B.

Strains of *N. meningitidis* are cultured on GC base agar (Difco, Detroit, Mich.) supplemented with 1% (w/v) IsoVitaleX enrichment (BBL, Cockeysville, Md.) (GcIsco agar) at 37° C. in an environment of air containing 3% $CO_2$. Meningococci were also cultured in liquid culture in GC broth supplemented with 1% (w/v) IsoVitaleX or in defined medium [Morse and Bartenstein (1974) *Proc. Soc. Exptl. Biol. Med.* 145:1418–1421]. Where necessary, tetracycline was added to the medium at a final concentration of 5 μg/ml to select for Tn916; when pAM120 or pAM170 transformants were selected, tetracycline was present at a concentration of 20 μg/ml. Where needed, spectinomycin was present in selective medium at a final concentration of 100 μg/ml. Stocks of meningococcal strains were stored at −70° C. in Trypticase Soy Broth (Difco) containing 20% glycerol.

*Escherichia coli* strains CG120 (pAM120) and CG170 (pAM170) were obtained from D. B. Clewell (University of Michigan, Ann Arbor, Mich.) and have been described [Gawron-Burke and Clewell (1984) *J. Bacteriol.* 159:214–221]. These plasmids are derived from pGL101 into which Tn916 was cloned. When these plasmids are introduced into neisserial cells and tetracycline resistance is selected, cells into which all or a part of the transposon has inserted are isolated. HaeIII and/or other restriction analysis and Southern hybridization to characterize the insertions as to the Class I or Class II type as described in Stephens et al. (1991) *Infect. Immun.* 62:2947–2952. Tetracycline resistant *N. meningitidis* NMB derivatives are typically isolated at a frequency of about 10–7 per μg plasmid DNA.

*E. coli* cells were cultured in Luria-Bertani broth [Sambrook et al. (1989) supra] at 37° C. with aeration. Where necessary, tetracycline was added to the medium at a final concentration of 4 μg/ml.

*Neisseria meningtidis* NMB-469 and *Neisseria meningitidis* NMB-559 were deposited with the American Type Culture Collection, 12301 Parklawn Drive, Rockville, Md. 20852, on Sep. 19, 1997, and are identified by Accession Nos. ATCC202039 and ATCC202038, respectively. These deposits were made in accordance with the Budapest Treaty.

Example 2

Transposon Mutagenesis

Tn916 is introduced into *N. meningitidis* NMB by transformation as described [Kathariou et al. (1990) *Mol. Microbiol.* 4:729–735], and the presence of the transposon was selected in solid medium with tetracycline. Preferably, the mutants isolated are the result of Class II insertions as described hereinabove.

The genetic stability during growth and laboratory passage for each Tn916 insertion mutant strain was tested. Only mutants having the phenotype of drug resistance and truncated LOS as measured by negative reaction with monoclonal antibody 3F11 were selected if there was less than 1/1000 dissociation of the drug resistance and loss of antibody binding. Further confirmation of the association of the tetracycline resistance and LOS phenotype entailed the preparation of DNA fragments from the mutant, transformation into the parental *N. meningitidis* NMB with reproduction of the truncated LOS phenotype in the tetracycline-resistant transformants. The LOS phenotype is the result of homologous recombination via the DNA flanking the Tn916-derived portion of the DNA transformed into the parental strain.

Example 3

LOS Sample Preparation

LOS samples were prepared by Proteinase K digestion as described [Hitchcock and Brown (1983) *J. Bacteriol.* 154:269–277]. The bacteria were lysed in distilled water, and the concentration of total protein ($\mu$g/ml) was determined by the Bradford method (Bio-Rad, Hercules, Calif.). Proteinase K digestion was performed as follows: 1 $\mu$g total protein was added to 9 $\mu$l 2% SDS and 2 $\mu$l 25 mg/ml Proteinase K. The reaction was stopped by the addition of loading buffer (1 M Tris-HCl, pH 8.6, 10% glycerol, 2% SDS, 5% $\beta$-mercaptoethanol, 0.05% bromophenol blue).

LOS is also prepared by a modification of the published procedure of Galanos et al. (1969) *Eur. J. Biochem.* 9:245–249. Bacterial cells of the desired strain are grown in 8 l GC broth for 18 hrs in a shaking incubator (New Brunswick Scientific Co., Inc., Edison, N.J.). Cells are harvested and air dried in a SpeedVac (Savant Instruments, Inc., Farmingdale, N.Y.). 5 g (dry weight) cells are thoroughly suspended in 50 ml of LOS extraction solvent (90% phenol:chloroform:petroleum ether, 2:5:8) and then homogenized for 4 min using an Ultra Turmax Tissumizer (Janke and Tunkel). This mixture is stirred for 2 hrs, and then it is centrifuged at 10,500×g for 15 min at 4° C. The supernatant is collected, and the extraction of the pelleted material is repeated as above in LOS solvent. The two supernatants are then pooled, and the final pellet is discarded. The petroleum ether and chloroform are removed by rotary evaporation for 1 hr using a Model RE-II rotary evaporator (Buchel) with a water bath temperature of 40° C. The residual phenol phase is chilled on ice, and the LOS is precipitated by the addition of 6 volumes of cold diethyl ether:acetone (1:5). The white precipitate is collected as a pellet after centrifugation at 5000×g for 10 min at 4° C. The supernatant is discarded, and the pellet is washed three times with 80% phenol and then two washed with petroleum ether, The pellet is dried in the SpeedVac overnight, then resuspended in distilled water and aliquoted into eppendorf tubes. These samples are dried in the SpeedVac as before are stored at 4° C. This procedure generally yields about 60 mg LOS from 5 g (dry weight) of bacterial cells.

Example 4

SDS PAGE Analysis

Tricine-SDS polyacrylamide gels (14% acrylamide) were prepared as previously outline [Schagger and von Jagow (1987) *Anal. Biochem.* 166:368–379] using the mini-Protean II apparatus (BioRad, Hercules, Calif.). Each sample is heated to 100° C. for 4 minutes before loading. About 125 ng total protein is loaded per lane. The sample is electrophoresed at 30 V through the stacking gel and at 95 V through the separating gel. Prestained low molecular weight markers (Boehringer Mannheim, Indianapolis, Ind.) were used. Bands were visualized using the silver staining method as described in Hitchcock and Brown (1983) supra.

Example 5

Immunological Techniques and Reagents

Monoclonal antibody (mAb) 3F11 is specific for the terminal galactose residue of the lacto-N-neotetraose unit (Gal$\beta$1-4GlcNac$\beta$1-3Gal$\beta$1-4Glc$\beta$1-4Hep$_2$-KDO$_2$-Lipid A) which is expressed as part of the L3 immunotype of NMB. mAb 3F11 was obtained from Michael Apicella of the University of Iowa, Iowa City, Iowa). This antibody has been described in Apicella et al. (1981) *Infect. Immun.* 34:751–756. mAb SC1-3 specifically recognizes the group B capsule of *N. meningitidis*; it was obtained from W. Zollinger (Walter Reed Institute of Research, Washington, D.C.). Other monoclonal antibodies specific for the group B capsule have been described, and polyclonal antibody specific for the group B capsule can also be used.

Immunoblots were performed as described in Kathariou et al. (1990) supra.

Example 6

Bactericidal Serum Killing Assays

Strains used in the assays were grown to mid-logarithmic phase ($OD_{550}$=0.5) in 10 ml GC broth aerated at 250 rpm. Bacterial density was adjusted to $1\times10^5$ cfu/ml using the approximation of an $OD_{550}$ of 1 is equivalent to $2\times10^8$ cfu/ml. 50 mM HEPES MEM (pH 7.3) [Stephens and Shager (1987) *Journal of Gen. Microbiol.* 133:1671–2679] is used as diluent for bacterial cultures and for normal human serum (NHS). Collection and analysis of NHS has been described [Stephens and Shafer (1987) supra]. The bactericidal assays contained 100 μl NHS to which 10 μl of $1\times10^5$ cfu/ml of the desired bacterial strain was added. Controls consisted of 100 μl of heat-treated NHS (30 min at 60° C.) with bacteria, and zero-time controls contained 100 μl 50 mM HEPES MEM with bacteria. Two aliquots of 10 μl each are taken from each assay at each time point and spread on half agar plates to determine viable cell numbers. Time course experiments, although performed on the same day, were individually prepared (i.e., a fresh dilution is prepared from the original broth culture before each set of assays). Zero time points show that there is no loss of viability in both cultures as compared to the dilutions made in 50 mM HEPES MEM, which decreased steadily over time. The results are expressed as percentage survival, and the results are plotted on a logarithmic scale. See FIGS. 2A–2F. Both *N. meningitidis* NMB and mutant NMB-R6 are resistant to 10% NHS. Mutant NMB-559 is significantly more sensitive to 10% NHS (30 min incubation) than strains NMB and NMB-R6. Cap⁻ NMB-M7 is completely killed after 15 min. incubation. Assays in 25% NHS reveal that R6 and 559 are sensitive under these conditions (>log decrease in viability after 30 min incubation) but the difference from NMB was not statistically significant. Cap⁻ NMB-M7 (capsule-deficient) was significantly more sensitive than parental NMB and the truncated LOS mutants (four logs of killing after 5 min incubation).

Example 7

DNA Sequencing

For determination of the sequence flanking the Tn916-derived insertion, the fragment of DNA comprising the insertion is cloned into a suitable plasmid vector, for example after HaeIII digestion of chromosomal DNA. Double-stranded DNA was subcloned and sequenced by the dideoxy chain termination method [Sanger et al. (1977) *Proc. Natl. Acad. Sci.* USA 74, 5463–5467], for example using sequencing kits purchased from United States Biochemical Corporation (Cleveland, Ohio). Oligonucleotide primers for sequencing reactions are synthesized by the phosphoramidite method with an Applied Biosystems model 394 automated DNA synthesizer (Applied Biosystems, Foster City, Calif.), purified by PAGE and desalted on Sep-Pak (Millipore Corp., Beverly, Mass.) using standard protocols.

TABLE 1

Amino Acid Sequence Comparison of nlaB and plsC Gene Products

```
          Gap Weight:   3.000        Average Match:    0.540
       Length Weight:   0.100     Average Mismatch:   -0.396
             Quality: 108.8                 Length:     380
               Ratio:   0.444                 Gaps:       7
   Percent Similarity:  44.726     Percent Identity:  27.004
nlaB.pro x plsceco.pro ..

nlaB        MHAKMHRLVRTGRRRNQRHLVLPAHRCRNCNCRKPKPGMIEDIIAVQRQP nlaB        SEPGWSATACAICRQSMPSAETRAGSDRKRQKNALPTRSRITRTHTGFRY nlaB.pro    LARFLTIHHAGKRRTASRLNIPHFRQGKTMLIIRNLIYWLILCSTLIFLF
                            ||.| .||.  :::|.|: :|
plsc.pro    ............................MLYIFRLII.TVIYSILVCVF nlaB.pro    PFMLPAFPGRGAQDARVWVKILNLSLKHIVGLKY...RIIGAENIPDRRA
            . :.. |..|.:... .:..::. .|  .:.|||    : .:||...: |
plsc.pro    GSIYCLFSPRNPKHVATFGHMFG.RLAPLFGLKVECRKPTDAESYGN..A nlaB.pro    VICAKHQTA.GKRSPFRTIFPPQVYVAKRELFKIPFFGWGLKLVKTIGID
            :..|.||.. :.  .:  ..:  ||  |  |:|:.|:.|||||   ..|.  .: ||
plsc.pro    IYIANHQNNYDMVTASNIVQPPTVTVGKKSLLWIPFFGQLYWLTGNLLID nlaB.pro    RNNRREANEQLIKQGLARKNEGYWITIFPEGTRLAPGKRGKYKLGGARMA
            ||||  .|:: :  . .    |.   ..| :|||||||  .   .:|  |: :  |
plsc.pro    RNNRTKAHGTIAEVVNHFKKRRISIWMFPEGTRSRGRGLLPFKTGAFHAA nlaB.pro    KMFEMDIVPVALNSDEFWPKNSFLKYPGEITVVICPTIPHASGSEA..EL
            ::.|:||.:....  . . |..  |. ::.|. . . |.:.  ||
plsc.pro    IAAGVPIIPVCVSTTSNKINLNRLHNGLVIVEMLPPIDVSQYGKDQVREL nlaB.pro    MGKCEHLIETQQPLISGARPVCRQNAV*..  (SEQ ID NO:4)
            :.|   ::|   |.:  . .:.|.  .:|.
plsc.pro    AAHCRSIME..QKIAELDKEVAEREAAGKV  (SEQ ID NO:5)
```

Amino acid sequence alignment of nlaB ORF4 with plsC of *E. coli* by the method of Needleman and Wunsch (Needleman and Wunsch, 1970). Lines indicate identical residues, double dots indicate similar residues and single dots indicate residues that are somewhat similar.

We claim:

1. A genetically stable mutant of a neisserial strain in which a gene selected from the group consisting of a gene encoding α-1,2-N-acetylglucosamine transferase which has been inactivated and an nlaB gene has been inactivated.

2. The genetically stable mutant of claim 1 wherein said neisserial strain is a strain of *Neisseria meningitidis*.

3. The genetically stable mutant of claim 1 wherein said gene encoding α-1,2-N-acetylglucosamine transferase has been inactivated.

4. The genetically stable mutant of claim 3 which is *N. meningitidis* NMB-559.

5. The genetically stable mutant of claim 1 wherein said nlaB gene has been inactivated.

6. The genetically stable mutant of claim 5 which is

UNITED STATES PATENT AND TRADEMARK OFFICE
CERTIFICATE OF CORRECTION

PATENT NO. : 5,976,536

DATED : November 2, 1999

INVENTOR(S) : Stephens and Kahler

It is certified that error appears in the above-identified patent and that said Letters Patent is hereby corrected as shown below:

On the Title Page, in the Abstract, in the sixth line, please insert --mutation-- in between "stable" and "in".
In Column 5, line 63, please delete "is" and replace with --in--.
In Column 11, line 57, please delete the "a" between "immunizing" and "humans,".
In Column 12, line 24, please delete "understand" and replace with --understood--.
In Column 14, line 63, please delete "10-7" and replace with --$10^{-7}$--.
In Column 16, line 14, please delete "outline" and replace with --outlined--.
In Column 18, in Table 1, the sixth line after the title of the table, please change this line:
   "nlaB.pro x plsceco.pro .." to the following: --nlaB.pro x plsc_eco.pro ..--.

Signed and Sealed this

Fifth Day of September, 2000

Q. TODD DICKINSON

*Attest:*

*Attesting Officer*  *Director of Patents and Trademarks*

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 1065 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (vi) ORIGINAL SOURCE:
        (A) ORGANISM: Neisseria meningitidis
        (B) STRAIN: NMB (ix) FEATURE:
        (A) NAME/KEY: CDS
        (B) LOCATION: 1..1065

(xi) SEQUENCE DESCRIPTION: SEQ ID NO:1:

```
ATG GAA AAA GAA TTC AGG ATA TTA AAT ATC GTA TCG GCC AAG ATT TGG        48
Met Glu Lys Glu Phe Arg Ile Leu Asn Ile Val Ser Ala Lys Ile Trp
 1               5                  10                  15

GGT GGG GGC GAA CAA TAT GTC TAT GAT GTT TCA AAA GCA TTG GGG CTT        96
Gly Gly Gly Glu Gln Tyr Val Tyr Asp Val Ser Lys Ala Leu Gly Leu
             20                  25                  30

CGG GGC TGC ACA ATG TTT ACC GCC GTC AAT AAA AAT AAT GAG TTG ATG       144
Arg Gly Cys Thr Met Phe Thr Ala Val Asn Lys Asn Asn Glu Leu Met
         35                  40                  45

CAC AGA CGC TTT TCC GAA GTT TCT TCC GTT TTC ACG ACA CGC CTT CAC       192
His Arg Arg Phe Ser Glu Val Ser Ser Val Phe Thr Thr Arg Leu His
     50                  55                  60

ACG CTC AAC GGG CTG TTT TCG CTC TGC GCG CTT ACC CGC TTT ATC CGG       240
Thr Leu Asn Gly Leu Phe Ser Leu Cys Ala Leu Thr Arg Phe Ile Arg
 65                  70                  75                  80

GAA AAC CGC ATT TCC CAC CTG ATG ATA CAC ACC GGC AAA ATT GCC GCC       288
Glu Asn Arg Ile Ser His Leu Met Ile His Thr Gly Lys Ile Ala Ala
                 85                  90                  95

TTA TCC ATA CTT TTG AAA AAA CTG ACC GGG GTG CGC CTG ATA TTT GTC       336
Leu Ser Ile Leu Leu Lys Lys Leu Thr Gly Val Arg Leu Ile Phe Val
            100                 105                 110

AAA CAT AAT GTC GTC GCC AAC AAA ACC GAT TTT TAC CAC CGC CTG ATA       384
Lys His Asn Val Val Ala Asn Lys Thr Asp Phe Tyr His Arg Leu Ile
        115                 120                 125

CAG AAA AAC ACA GAC CGC TTT ATT TGC GTT TCC CGT CTG GTT TAC GAT       432
Gln Lys Asn Thr Asp Arg Phe Ile Cys Val Ser Arg Leu Val Tyr Asp
    130                 135                 140

GTG CAA ACC GCC GAC AAT CCC TTT AAA GAA AAA TAC CGG ATT ATT CAT       480
Val Gln Thr Ala Asp Asn Pro Phe Lys Glu Lys Tyr Arg Ile Ile His
145                 150                 155                 160

AAC GGT ATC GAT ACC GAT CGG TTC CCT CCC TCT CAA GAA AAA CCC GAC       528
Asn Gly Ile Asp Thr Asp Arg Phe Pro Pro Ser Gln Glu Lys Pro Asp
                165                 170                 175

AGC CGT TTT TTT ACC GTC GCC TAC GCC GGC AGG ATC AGT CCG GAA AAA       576
Ser Arg Phe Phe Thr Val Ala Tyr Ala Gly Arg Ile Ser Pro Glu Lys
            180                 185                 190
```

```
GGA TTG GAA AAC CTA ATT GAA GCC TGT GTG ATA TTG CAT CGG AAA TAT          624
Gly Leu Glu Asn Leu Ile Glu Ala Cys Val Ile Leu His Arg Lys Tyr
            195                 200                 205

CCT CAA ATC AGA CTC AAA TTG GCA GGG CAC GGA CAT CCT GAT TAT ATG          672
Pro Gln Ile Arg Leu Lys Leu Ala Gly His Gly His Pro Asp Tyr Met
210                 215                 220

TGC CGC CTG AAG CGG GAC GTA TCT GCT TCA GGA GCA GAA CCA TTT GTT          720
Cys Arg Leu Lys Arg Asp Val Ser Ala Ser Gly Ala Glu Pro Phe Val
225                 230                 235                 240

TCT TTT GAA GGG TTT ACC GAA AAC ATT GCT TCG TTT TAC CGC CAA AGC          768
Ser Phe Glu Gly Phe Thr Glu Asn Ile Ala Ser Phe Tyr Arg Gln Ser
            245                 250                 255

GAT GTC GTG GTT TTG CCC AGC CTC GTC CCG GAG GCA TTC GGT TTG TCA          816
Asp Val Val Val Leu Pro Ser Leu Val Pro Glu Ala Phe Gly Leu Ser
                260                 265                 270

TTA TGC GAG GCG ATG TAC TGC CGA ACG GCG GTG ATT TCC AAT ACT TTG          864
Leu Cys Glu Ala Met Tyr Cys Arg Thr Ala Val Ile Ser Asn Thr Leu
            275                 280                 285

GGG GCG CAA AAG GAA ATT GTC GAA CAT CAT CAA TCG GGG ATT CTG CTG          912
Gly Ala Gln Lys Glu Ile Val Glu His His Gln Ser Gly Ile Leu Leu
290                 295                 300

GAT AGG CTT ACG CCT GAA TCT TTG GCG GAC GAA ATC GAA CGC CTC GTC          960
Asp Arg Leu Thr Pro Glu Ser Leu Ala Asp Glu Ile Glu Arg Leu Val
305                 310                 315                 320

TTA AAC CCC GAA GCA AAA AAC GCA CTG GCA ACG GCA GCT CAT CAA TGC         1008
Leu Asn Pro Glu Ala Lys Asn Ala Leu Ala Thr Ala Ala His Gln Cys
                325                 330                 335

GTC GCC GCC CGT TTT ACC ATC AAC CAT ACC GCC GAC AAA TTA TTG GAT         1056
Val Ala Ala Arg Phe Thr Ile Asn His Thr Ala Asp Lys Leu Leu Asp
            340                 345                 350

GCA ATA TAA                                                             1065
Ala Ile *
        355

(2) INFORMATION FOR SEQ ID NO:2:

(i) SEQUENCE CHARACTERISTICS:
        (A) LENGTH: 354 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Lys Glu Phe Arg Ile Leu Asn Ile Val Ser Ala Lys Ile Trp
1                   5                  10                  15

Gly Gly Gly Glu Gln Tyr Val Tyr Asp Val Ser Lys Ala Leu Gly Leu
                20                  25                  30

Arg Gly Cys Thr Met Phe Thr Ala Val Asn Lys Asn Asn Glu Leu Met
            35                  40                  45

His Arg Arg Phe Ser Glu Val Ser Ser Val Phe Thr Thr Arg Leu His
        50                  55                  60

Thr Leu Asn Gly Leu Phe Ser Leu Cys Ala Leu Thr Arg Phe Ile Arg
65                  70                  75                  80

Glu Asn Arg Ile Ser His Leu Met Ile His Thr Gly Lys Ile Ala Ala
                85                  90                  95

Leu Ser Ile Leu Leu Lys Lys Leu Thr Gly Val Arg Leu Ile Phe Val
            100                 105                 110

Lys His Asn Val Val Ala Asn Lys Thr Asp Phe Tyr His Arg Leu Ile
        115                 120                 125
```

```
Gln Lys Asn Thr Asp Arg Phe Ile Cys Val Ser Arg Leu Val Tyr Asp
    130                 135                 140
Val Gln Thr Ala Asp Asn Pro Phe Lys Glu Lys Tyr Arg Ile Ile His
145                 150                 155                 160
Asn Gly Ile Asp Thr Asp Arg Phe Pro Pro Ser Gln Glu Lys Pro Asp
                165                 170                 175
Ser Arg Phe Phe Thr Val Ala Tyr Ala Gly Arg Ile Ser Pro Glu Lys
            180                 185                 190
Gly Leu Glu Asn Leu Ile Glu Ala Cys Val Ile Leu His Arg Lys Tyr
        195                 200                 205
Pro Gln Ile Arg Leu Lys Leu Ala Gly His Gly His Pro Asp Tyr Met
210                 215                 220
Cys Arg Leu Lys Arg Asp Val Ser Ala Ser Gly Ala Glu Pro Phe Val
225                 230                 235                 240
Ser Phe Glu Gly Phe Thr Glu Asn Ile Ala Ser Phe Tyr Arg Gln Ser
                245                 250                 255
Asp Val Val Leu Pro Ser Leu Val Pro Glu Ala Phe Gly Leu Ser
            260                 265                 270
Leu Cys Glu Ala Met Tyr Cys Arg Thr Ala Val Ile Ser Asn Thr Leu
        275                 280                 285
Gly Ala Gln Lys Glu Ile Val Glu His His Gln Ser Gly Ile Leu Leu
290                 295                 300
Asp Arg Leu Thr Pro Glu Ser Leu Ala Asp Glu Ile Glu Arg Leu Val
305                 310                 315                 320
Leu Asn Pro Glu Ala Lys Asn Ala Leu Ala Thr Ala His Gln Cys
                325                 330                 335
Val Ala Ala Arg Phe Thr Ile Asn His Thr Ala Asp Lys Leu Leu Asp
            340                 345                 350
Ala Ile
    355
```

(2) INFORMATION FOR SEQ ID NO:3:

(i) SEQUENCE CHARACTERISTICS:
        (A) LENGTH: 729 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Neisseria meningitidis
        (B) STRAIN: NMB (ix) FEATURE:
        (A) NAME/KEY: CDS
        (B) LOCATION: 1..729

(xi) SEQUENCE DESCRIPTION: SEQ ID NO:3:

```
ATG CTC ATC ATC CGC AAC CTG ATT TAC TGG CTG ATA CTC TGT TCC ACC        48
Met Leu Ile Ile Arg Asn Leu Ile Tyr Trp Leu Ile Leu Cys Ser Thr
                    360                 365                 370

CTG ATT TTC CTC TTT CCC TTT ATG CTG CCT GCC TTT CCG GGA CGG GGC        96
Leu Ile Phe Leu Phe Pro Phe Met Leu Pro Ala Phe Pro Gly Arg Gly
            375                 380                 385
```

```
GCA CAA GAT GCG CGG GTC TGG GTC AAA ATC CTC AAC CTC TCG CTC AAA      144
Ala Gln Asp Ala Arg Val Trp Val Lys Ile Leu Asn Leu Ser Leu Lys
        390                 395                 400

CAC ATC GTC GGG CTC AAA TAC CGC ATC ATC GGC GCG GAA AAC ATC CCC      192
His Ile Val Gly Leu Lys Tyr Arg Ile Ile Gly Ala Glu Asn Ile Pro
405                 410                 415

GAC CGC CCC GCC GTC ATC TGC GCC AAA CAC CAA ACG GCT GGG AAA CGC      240
Asp Arg Pro Ala Val Ile Cys Ala Lys His Gln Thr Ala Gly Lys Arg
420                 425                 430                 435

TCG CCC TTC AGG ACA ATT TTT CCG CCG CAG GTT TAC GTT GCC AAA CGC      288
Ser Pro Phe Arg Thr Ile Phe Pro Pro Gln Val Tyr Val Ala Lys Arg
                440                 445                 450

GAG TTG TTC AAA ATC CCC TTT TTC GGC TGG GGC TTG AAA CTG GTC AAA      336
Glu Leu Phe Lys Ile Pro Phe Phe Gly Trp Gly Leu Lys Leu Val Lys
            455                 460                 465

ACC ATA GGC ATA GAC CGC AAC AAC CGC CGC GAA GCC AAC GAG CAG CTC      384
Thr Ile Gly Ile Asp Arg Asn Asn Arg Arg Glu Ala Asn Glu Gln Leu
        470                 475                 480

ATA AAA CAG GGG TTG GCG CGC AAA AAC GAA GGC TAT TGG ATT ACC ATT      432
Ile Lys Gln Gly Leu Ala Arg Lys Asn Glu Gly Tyr Trp Ile Thr Ile
485                 490                 495

TTC CCC GAA GGC ACG CGC CTT GCA CCC GGA AAG CGC GGC AAA TAC AAA      480
Phe Pro Glu Gly Thr Arg Leu Ala Pro Gly Lys Arg Gly Lys Tyr Lys
500                 505                 510                 515

CTC GGC GGC GCG CGC ATG GCG AAA ATG TTT GAG ATG GAC ATC GTC CCC      528
Leu Gly Gly Ala Arg Met Ala Lys Met Phe Glu Met Asp Ile Val Pro
                520                 525                 530

GTC GCC CTC AAC AGC GGC GAA TTT TGG CCG AAA AAC TCC TTT CTG AAA      576
Val Ala Leu Asn Ser Gly Glu Phe Trp Pro Lys Asn Ser Phe Leu Lys
            535                 540                 545

TAT CCG GGG GAA ATC ACC GTC GTC ATC TGT CCG ACC ATC CCG CAC GCA      624
Tyr Pro Gly Glu Ile Thr Val Val Ile Cys Pro Thr Ile Pro His Ala
        550                 555                 560

AGC GGC AGC GAA GCC GAA TTG ATG GGA AAA TGC GAA CAC CTC ATC GAA      672
Ser Gly Ser Glu Ala Glu Leu Met Gly Lys Cys Glu His Leu Ile Glu
565                 570                 575

ACG CAG CAG CCG CTC ATT TCC GGC GCA CGG CCC GTT TGC CGC CAA AAT      720
Thr Gln Gln Pro Leu Ile Ser Gly Ala Arg Pro Val Cys Arg Gln Asn
580                 585                 590                 595

GCC GTC TGA                                                          729
Ala Val *

(2) INFORMATION FOR SEQ ID NO:4:

(i) SEQUENCE CHARACTERISTICS:
        (A) LENGTH:  242 amino acids
        (B) TYPE: amino acid
        (D) TOPOLOGY: linear (ii) MOLECULE TYPE: protein (xi) SEQUENCE DESCRIPTION: SEQ ID NO:4:

Met Leu Ile Ile Arg Asn Leu Ile Tyr Trp Leu Ile Leu Cys Ser Thr
 1               5                  10                  15

Leu Ile Phe Leu Phe Pro Phe Met Leu Pro Ala Phe Pro Gly Arg Gly
            20                  25                  30

Ala Gln Asp Ala Arg Val Trp Val Lys Ile Leu Asn Leu Ser Leu Lys
        35                  40                  45

His Ile Val Gly Leu Lys Tyr Arg Ile Ile Gly Ala Glu Asn Ile Pro
    50                  55                  60
```

```
Asp Arg Pro Ala Val Ile Cys Ala Lys His Gln Thr Ala Gly Lys Arg
 65                  70                  75                  80

Ser Pro Phe Arg Thr Ile Phe Pro Pro Gln Val Tyr Val Ala Lys Arg
                 85                  90                  95

Glu Leu Phe Lys Ile Pro Phe Phe Gly Trp Gly Leu Lys Leu Val Lys
                100                 105                 110

Thr Ile Gly Ile Asp Arg Asn Asn Arg Arg Glu Ala Asn Glu Gln Leu
                115                 120                 125

Ile Lys Gln Gly Leu Ala Arg Lys Asn Glu Gly Tyr Trp Ile Thr Ile
130                 135                 140

Phe Pro Glu Gly Thr Arg Leu Ala Pro Gly Lys Arg Gly Lys Tyr Lys
145                 150                 155                 160

Leu Gly Gly Ala Arg Met Ala Lys Met Phe Glu Met Asp Ile Val Pro
                165                 170                 175

Val Ala Leu Asn Ser Gly Glu Phe Trp Pro Lys Asn Ser Phe Leu Lys
                180                 185                 190

Tyr Pro Gly Glu Ile Thr Val Val Ile Cys Pro Thr Ile Pro His Ala
                195                 200                 205

Ser Gly Ser Glu Ala Glu Leu Met Gly Lys Cys Glu His Leu Ile Glu
                210                 215                 220

Thr Gln Gln Pro Leu Ile Ser Gly Ala Arg Pro Val Cys Arg Gln Asn
225                 230                 235                 240

Ala Val (2) INFORMATION FOR SEQ ID NO:5:

(i) SEQUENCE CHARACTERISTICS:
        (A) LENGTH: 245 amino acids
        (B) TYPE: amino acid
        (C) STRANDEDNESS:
        (D) TOPOLOGY: linear (ii) MOLECULE TYPE: protein (iii) HYPOTHETICAL: NO (vi) ORIGINAL SOURCE:
        (A) ORGANISM: Escherichia coli (xi) SEQUENCE DESCRIPTION: SEQ ID NO:5:

Met Leu Tyr Ile Phe Arg Leu Ile Ile Thr Val Ile Tyr Ser Ile Leu
1                5                  10                  15

Val Cys Val Phe Gly Ser Ile Tyr Cys Leu Phe Ser Pro Arg Asn Pro
                 20                  25                  30

Lys His Val Ala Thr Phe Gly His Met Phe Gly Arg Leu Ala Pro Leu
                 35                  40                  45

Phe Gly Leu Lys Val Glu Cys Arg Lys Pro Thr Asp Ala Glu Ser Tyr
 50                  55                  60

Gly Asn Ala Ile Tyr Ile Ala Asn His Gln Asn Asn Tyr Asp Met Val
 65                  70                  75                  80

Thr Ala Ser Asn Ile Val Gln Pro Pro Thr Val Thr Val Gly Lys Lys
                 85                  90                  95

Ser Leu Leu Trp Ile Pro Phe Phe Gly Gln Leu Tyr Trp Leu Thr Gly
                100                 105                 110

Asn Leu Leu Ile Asp Arg Asn Asn Arg Thr Lys Ala His Gly Thr Ile
                115                 120                 125

Ala Glu Val Val Asn His Phe Lys Lys Arg Arg Ile Ser Ile Trp Met
                130                 135                 140
```

-continued

```
Phe Pro Glu Gly Thr Arg Ser Arg Gly Arg Gly Leu Leu Pro Phe Lys
145                 150                 155                 160

Thr Gly Ala Phe His Ala Ala Ile Ala Ala Gly Val Pro Ile Ile Pro
            165                 170                 175

Val Cys Val Ser Thr Thr Ser Asn Lys Ile Asn Leu Asn Arg Leu His
            180                 185                 190

Asn Gly Leu Val Ile Val Glu Met Leu Pro Pro Ile Asp Val Ser Gln
        195                 200                 205

Tyr Gly Lys Asp Gln Val Arg Glu Leu Ala Ala His Cys Arg Ser Ile
    210                 215                 220

Met Glu Gln Lys Ile Ala Glu Leu Asp Lys Glu Val Ala Glu Arg Glu
225                 230                 235                 240

Ala Ala Gly Lys Val
            245
```